United States Patent [19]

Jessup

[11] 4,405,308
[45] Sep. 20, 1983

[54] ANESTHESIA DEVICE WITH SELECTIVE SPRAY PORTS

[75] Inventor: James L. Jessup, Elk Grove Village, Ill.

[73] Assignee: The Kendall Company, Boston, Mass.

[21] Appl. No.: 334,029

[22] Filed: Dec. 23, 1981

[51] Int. Cl.³ .................... A61M 11/00; A61M 25/00
[52] U.S. Cl. ...................................... 604/200; 604/54;
604/239; 604/244; 604/256; 128/207.14;
128/200.22
[58] Field of Search .............................. 604/49, 51–54,
604/93, 187, 191, 218, 232, 239, 247–250, 256,
280, 283, 200; 128/207.14, 200.22

[56] References Cited

U.S. PATENT DOCUMENTS 1,531,213  3/1925  Nimmer .......................... 604/256 X
3,885,561  5/1975  Cami ................................... 604/247
4,182,326  1/1980  Ogle ................................... 604/203

Primary Examiner—Dalton L. Truluck
Attorney, Agent, or Firm—Powell L. Sprunger

[57] ABSTRACT

An anesthesia device comprising, a syringe having a chamber, and a device for pumping fluid from the chamber. The device has an elongated cannula attached to the syringe, with the cannula having a lumen in communication with the chamber of the syringe, a plurality of apertures in a distal portion of the cannula communicating with the lumen, and an opening adjacent a distal end of the cannula and distal the apertures, with the opening communicating with the lumen. The device has an element for releasably closing the apertures in the distal portion of the cannula while leaving the opening unobstructed, and for frictionally engaging the cannula to prevent dislodgment during use of the cannula.

4 Claims, 7 Drawing Figures

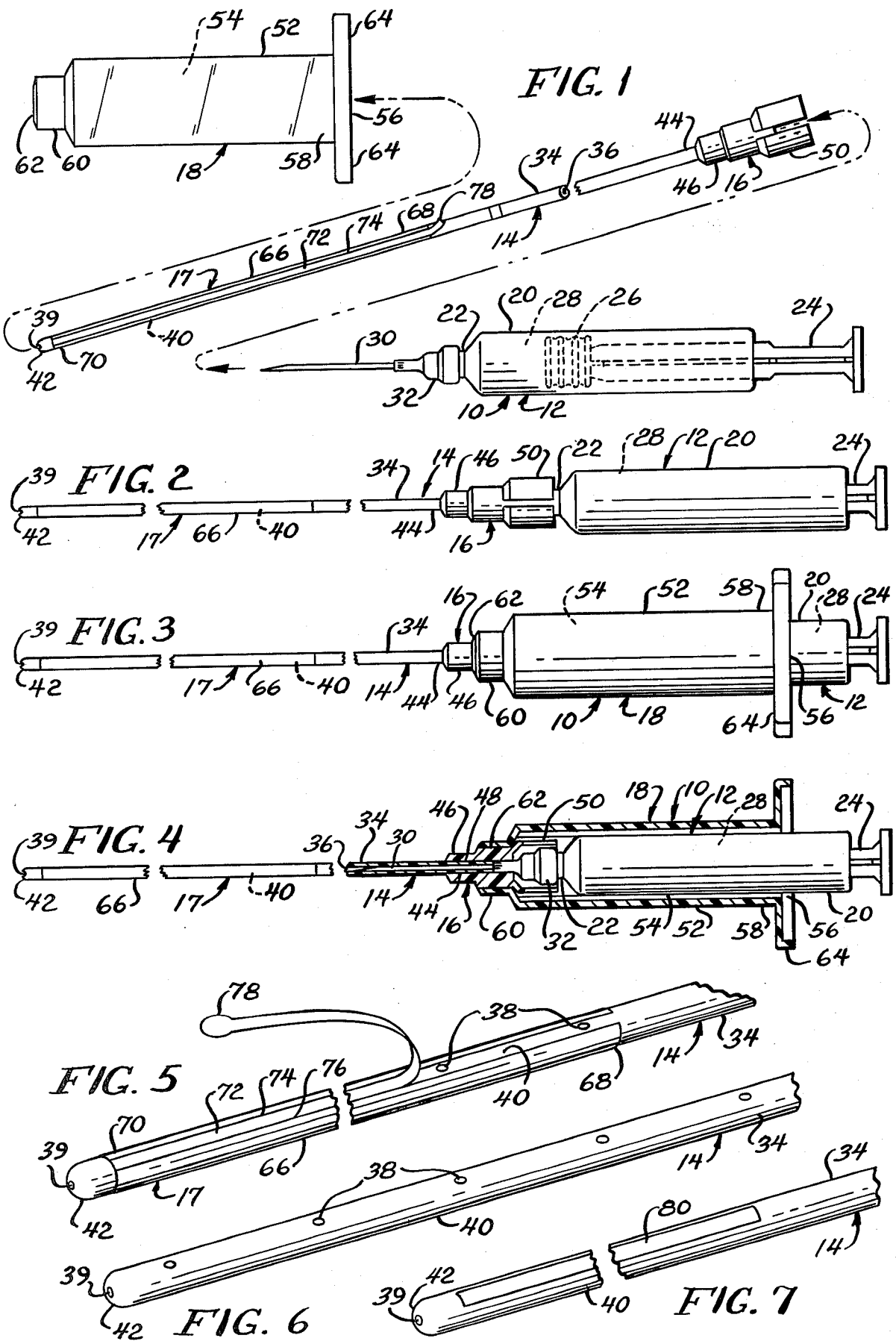

ANESTHESIA DEVICE WITH SELECTIVE SPRAY PORTS

BACKGROUND OF THE INVENTION

The present invention relates to anesthesia devices.

Before the present invention, it has been a common practice to apply an anesthetic drug to the trachea of a patient prior to endotracheal intubation or bronchoscopy. In one such laryngotracheal procedure, a cannula is inserted down the throat into the trachea after which the trachea is sprayed with the anesthetic drug. However, prior to the laryngotracheal procedure the back of the throat is sprayed with a topical anesthetic in order to facilitate the laryngotracheal procedure, particularly on a patient who is awake. In the past, an atomizer has been used to spray the throat, and a separate device is then used for the laryngotracheal procedure.

SUMMARY OF THE INVENTION

A principal feature of the present invention is the provision of an improved anesthesia device of simplified construction.

The anesthesia device comprises, a syringe having a chamber, and means for pumping fluid from the chamber. The device has an elongated cannula attached to the syringe, with the cannula having a lumen in communication with the chamber of the syringe, a plurality of apertures in a distal portion of the cannula communicating with the lumen, and an opening adjacent a distal end of the cannula and distal the apertures, with the opening communicating with the lumen. The device has means for releasably closing the apertures in the distal portion of the cannula while leaving the opening unobstructed.

A feature of the present invention is that the syringe may be pumped to eject an anesthetic drug from the syringe chambers through the distal opening onto the back of the patient's throat preparatory to a laryngotracheal anesthesia procedure.

Another feature of the invention is that the closing means frictionally engages the cannula to prevent dislodgment during use of the cannula to spray the back of the patient's throat.

Yet another feature of the invention is that the closing means may be removed from the cannula in order to expose the apertures, and the cannula may be inserted down the patient's throat in order to spray the trachea of the patient with the anesthetic drug through the apertures and opening.

Thus, a feature of the present invention is that the device may be used for a laryngotracheal procedure.

Accordingly, a feature of the present invention is that the device may be utilized for both purposes of spraying the back of the patient's throat and for a laryngotracheal procedure.

Further features will become more fully apparent in the following description of the embodiments of this invention and from the appended claims.

DESCRIPTION OF THE DRAWINGS

In the drawings:

FIG. 1 is an exploded fragmentary plan view of an anesthesia device of the present invention comprising a syringe, a cannula, an adapter, a sleeve on the cannula, and a holding member;

FIG. 2 is a fragmentary plan view showing the syringe attached to the adapter on the cannula;

FIG. 3 is a fragmentary plan view of the device showing the syringe and cannula inserted into the holding member;

FIG. 4 is a fragmentary plan view taken partly in section of the assembled device of FIG. 3;

FIG. 5 is a fragmentary perspective view illustrating the sleeve as partly removed from the cannula;

FIG. 6 is a fragmentary perspective view illustrating the cannula with the sleeve removed; and FIG. 7 is a fragmentary perspective view of another embodiment of the present invention.

DESCRIPTION OF THE PREFERRED EMBODIMENTS

Referring now to FIGS. 1 and 4-6, there is shown an anesthesia device generally designated 10 comprising a syringe 12, an elongated cannula 14, an adapter 16, a sleeve 17 on the cannula 14, and a holding member 18. The syringe 12 may be of the type comprising a hollow cylindrical barrel 20 defining a chamber 28, a tip 22 extending distally from the barrel 20, and a plunger 24 received in the barrel 20, with the plunger 24 having a distal head 26 of elastic material, such as rubber, received in the chamber 28 of the barrel 20 and engaging against an inner surface of the barrel 20. The syringe 12 has an elongated distal hollow needle 30, and a hub 32 securing a proximal end of the needle 30 to the tip 22 of the syringe 12. In use, the syringe plunger 24 is pumped in order to eject a liquid anesthetic drug from the chamber 28 through the distal needle 30.

The cannula 14 has a hollow wall 34 defining a lumen 36, a plurality of apertures 38 in a distal portion 40 of the cannula 14 communicating with the lumen 36, and an opening 39 at a distal end 42 of the cannula 14 and communicating with the lumen 36, with the opening 39 being located distal the apertures 38. The cannula 14 has a proximal end 44 attached to the adapter 16. The cannula 14 may be made of a suitable material, such as plastic.

The adapter 16 has a hollow distal tongue 46 defining a bore 48 which receives and securely engages the proximal end 44 of the cannula 14. The adapter 16 also has a proximal annular flange 50 for a purpose which will be described below.

The holding member 18 has a cylindrical wall 52 defining a cavity 54. The inner diameter of the wall 52 is slightly larger than the outer diameter of the syringe barrel 20, such that the syringe barrel 20 may be received in the cavity 54 of the holding member 18. The holding member 18 has an opening 56 at a proximal end 58 of the holding member 18, and an annular shoulder 60 of reduced diameter extending distally from the wall 52, with the shoulder 60 defining a distal opening 62. Also, the holding member 18 has an outwardly directed flange 64 at the proximal end 58 of the wall 52 defining finger grips for the holding member 18. As shown in FIG. 4, the flange 50 of the adapter 16 has a larger diameter than the inside diameter of the shoulder 60 of the holding member 18.

With reference to FIGS. 1, 5, and 6, the sleeve 17 comprises an elongated cylindrical wall 66 of flexible material, such as a suitable plastic material heatshrunk on the cannula 14, such that the wall 66 is snugly received on the cannula 14 and frictionally engages the cannula 14. As shown, the wall 66 has a proximal end 68 located proximal the apertures 38, and a distal end 70 located distal the apertures 38 and proximal the opening 39. Thus, the wall 66 covers and closes the apertures 38 of the cannula while leaving the opening 39 unobstructed. The sleeve 17 has an elongated tear strip 72 defined by a pair of score lines 74 and 76, such that the tear strip 72 extends longitudinally along the sleeve 17. As shown, the tear strip 72 may have a tab 78 at one end to facilitate use of the tear strip 72.

With reference to FIGS. 1 and 2, in use of the device 10, the needle 30 of the syringe 12 is inserted through the adapter 16 into the lumen 36 of the cannula 14, with the syringe hub 32 being received in the adapter 16. Next, with reference to FIGS. 3 and 4, the attached cannula 14 and syringe 12 are inserted into the cavity 54 of the holding member 18 until the holding member shoulder 60 snugly receives the adapter 16. In this configuration, the cannula 14 extends distally from the opening 62 of the holding member 18, with the syringe barrel 20 being received in the holding member cavity 54. As shown in FIG. 4, the flange 50 of the adapter 16 engages against an inner portion of the holding member shoulder 60 in order to releasably hold the adapter 16 and cannula 14 in place.

In this assembled configuration, the distal end 42 of the cannula 14 is inserted into the mouth of the patient adjacent the throat, and the syringe 12 is pumped in order to eject an anesthetic drug from the syringe chamber 28 through the needle 30 and cannula opening 39 onto the throat of the patient preparatory to a laryngotracheal anesthesia procedure. During this time, the sleeve 17 covers the apertures 38 of the cannula 14, and prevents the spraying of the anesthetic drug through the apertures 38. Also, the sleeve 17 frictionally engages the cannula 14 to prevent loss of the sleeve during this procedure.

After the throat has been sprayed, the cannula 14 is removed from the patient's mouth, and the tab 78 is utilized to pull the tear strip 72 from the sleeve 17, as shown in FIG. 5, in order to free and remove the sleeve 17 from the distal portion 40 of the cannula 14, thus exposing the apertures 38. Next, the distal portion 40 of the cannula 14 is inserted down the patient's throat, and the syringe 12 is pumped in order to eject an anesthetic drug from the syringe chamber 28 through the needle 30 and cannula apertures 38 and opening 39 onto the trachea of the patient in order to perform the laryngotracheal procedure preparatory to an endotracheal intubation or bronchoscopy. During this time, the proximal end 44 of the cannula 14, which is permanently bonded to adapter 16, is firmly held in holding member 18 in order to prevent loss of the cannula 14 down the patient's throat during the laryngotracheal procedure.

Thus, in accordance with the present invention, the anesthesia device 10 may be assembled in a simplified fashion for use in either spraying the back of the patient's throat or a laryngotracheal procedure with the sleeve 17 removed from the cannula 14.

Another embodiment of the present invention is illustrated in FIG. 7, in which like reference numerals designate like parts. In this embodiment, the cannula 14 has an elongated strip 80 of pressure-sensitive tape on the distal portion 40 of the cannula 14 in position to cover and close the apertures 38 of the cannula 14. The tape strip 80 frictionally engages the cannula 14 in order to prevent loss of the strip 80 while the patient's throat is being sprayed. After the patient's throat has been sprayed, the strip 80 may be peeled from the cannula 14 in order to expose the apertures 38 of the cannula 14. In other respects, the cannula 14 of FIG. 7 operates in a manner as previously discussed in connection with the cannula 14 of FIGS. 1-6.

The foregoing detailed description is given for clearness of understanding only, and no unnecessary limitations should be understood therefrom, as modifications will be obvious to those skilled in the art.

I claim:

1. An anesthesia device, comprising:
   a syringe having a chamber, and means for pumping fluid from the chamber;
   an elongated cannula attached to the syringe, said cannula having a lumen in communication with the chamber of the syringe, a plurality of apertures in a distal portion of the cannula communicating with the lumen, and an opening adjacent a distal end of the cannula and distal said apertures, said opening communicating with the lumen; and
   means for releasably closing the apertures in the distal portion of the cannula while leaving said opening unobstructed, and for frictionally engaging the cannula to prevent dislodgment during use of the cannula, wherein the closing means comprises an elongated sleeve of flexible material snugly received on the distal portion of the cannula over said apertures, wherein the sleeve has a tear strip extending longitudinally along the sleeve to sever the sleeve.

2. The device of claim 1 wherein said opening is at the distal end of the cannula.

3. A method of applying anesthesia to a patient with a device of the type comprising a syringe having a chamber, and means for pumping fluid from the chamber, an elongated cannula attached to the syringe, said cannula having a lumen in communication with the chamber of the syringe, a plurality of apertures in a distal portion of the cannula communicating with the lumen, and an opening adjacent a distal end of the cannula and distal the apertures, with the opening communicating with the lumen, and means for releasably closing the apertures in the distal portion of the cannula while leaving the opening unobstructed, said method comprising the steps of:
   inserting the distal end of the cannula into the patient's mouth and positioning the opening adjacent the patient's throat;
   pumping the syringe to eject an anesthetic drug from the syringe chamber through the opening onto the patient's throat;
   removing the closing means from the cannula;
   inserting the distal portion down the patient's throat until the apertures are located adjacent the trachea; and
   pumping the syringe to eject the anesthetic drug from the syringe chamber through the apertures onto the trachea.

4. An anesthesia device, comprising:
   a syringe having a chamber, and means for pumping fluid from the chamber;
   an elongated cannula attached to the syringe, said cannula having a lumen in communication with the chamber of the syringe, a plurality of apertures in a distal portion of the cannula communicating with the lumen, and an opening adjacent a distal end of the cannula and distal said apertures, said opening communicating with the lumen; and
   means for releasably closing the apertures in the distal portion of the cannula while leaving said opening unobstructed, and for frictionally engaging the cannula to prevent dislodgment during use of the cannula, wherein the closing means comprises an elongated strip of tape releasably attached to the cannula over the apertures.

* * * * *